United States Patent

Bagits et al.

[11] Patent Number: 5,556,398
[45] Date of Patent: Sep. 17, 1996

[54] EXTERNAL SELF-RETAINING AND STRESSED FIXATOR FOR FIXING LARGE TUBULAR BONES

[76] Inventors: Tibor Bagits, Lekai Janos ter 15, Budapest, Hungary, H-1124; Endre Cziffer, Bakatas u., Budapest, Hungary, H-1093; Mihaly Szacsky, Varosmajor u. 26/b, Budapest, Hungary, H-1122

[21] Appl. No.: 349,150

[22] Filed: Dec. 2, 1994

Related U.S. Application Data

[63] Continuation of Ser. No. 117,090, filed as PCT/HU92/00011, Mar. 5, 1992 published as WO92/15258, abandoned.

[30] Foreign Application Priority Data

Mar. 5, 1991 [HU] Hungary ................................. 702/91

[51] Int. Cl.⁶ ........................................................ A61B 17/64
[52] U.S. Cl. ...................................................... 606/59; 606/54
[58] Field of Search ................................. 606/53, 54, 57, 606/59, 105

[56] References Cited

U.S. PATENT DOCUMENTS 1,997,446  4/1935  Longfellow .
4,968,316  11/1990  Hergenroeder ............................ 606/57
4,969,886  11/1990  Cziffer et al. .

FOREIGN PATENT DOCUMENTS 0140786  5/1985  European Pat. Off. .
2174377  10/1973  France .

*Primary Examiner*—Guy Tucker
*Attorney, Agent, or Firm*—Pennie & Edmonds

[57] ABSTRACT

A disposable external fixator includes a rod and pins insertable therethrough and insertable into a fractured bone for fixation. The rod includes equidistantly spaced and aligned bores and ends provided with threads. The diameter of the bores is larger than the diameter of the pins. The fixator also includes two stretching tubes of relatively soft material slidably mountable onto the ends of the rod and having bores corresponding to the bores of the rod. Internally threaded closing pieces are screwable onto the threaded ends of the rod to axially displace the stretching tubes relative to the rod.

7 Claims, 4 Drawing Sheets

EXTERNAL SELF-RETAINING AND STRESSED FIXATOR FOR FIXING LARGE TUBULAR BONES

This is a continuation of application Ser. No. 08/117,090, filed as PCT/HU92/00011, Mar. 5, 1992 published as WO92/15258, now abandoned.

FIELD OF THE INVENTION

The present invention relates to a disposable external self-retaining and stressed fixator especially for fixing large tubular bones fractured due to traumatic lesions comprising means for receiving pins—or Kirschner-pins—known per se bored into the fractured bones as well as means for fixing them.

DESCRIPTION OF THE PRIOR ART

External fixators have extensively been used in surgery especially for treating traumatic lesions of large tubular bones. In this case it is an essential requirement to disburden the fractured bones by using an external fixator in order to make the lesioned part of the body at least partly loadable and the primary wound treatment possible in case of open fractures.

In 1984, Clayton Parkhill proposed for the first time to use external fixator frames made of metal. His method and proposal essentially consist in performing bone fixation spanning the fracture by boring pins into the healthy bone tissue and by applying variously constructed frames to the protruding ends of the pins. Goossens (in 1931) placed joints to the ends of the pins or nails thereby making possible joining up of the supporting elements. Judet (1934, 1959) succeeded in solving the problem of compression of the frames.

Several physicians (Bandl, Holz, Weller, Hoffman, Vidal of the AO Society (Arbeitsgesellschaft fur Osteosynthesefragen) worked our a rigid fixator frame in which screw clamping members are placed to the ends of the pins and nails and connected by rigid external rods creating hereby a complete, statically uniform bridging over.

The U.S. Pat. No. 4,969,886 describes a disposable fixator which is cheap, easy to handle and at the same time guarantees perfect external fixation of fractured small tubular bones. The fixator comprises a fixator rod made of soft aluminium thereby easily bendable to any desired form and containing a number of preferably equidistantly spaced bores of parallel axis. Into these bores can be introduced the standard pins known per se—the so-called Kirschner-pins—and are fixed in a strong binding made by squeezing and deforming the proximity of the bores.

SUMMARY OF THE INVENTION

The aim of the present invention is to treat traumatic lesions of large tubular bones and move exactly, to construct a disposable device comprising a few light, simple and cheap constituents and being easy to handle therefore attachment and fixation does not require special auxiliary means. The professional aim is—of course—to make the work of traumatologists, surgeons and veterinary surgeons significantly easier. It is an important requirement to construct a fixator suitable also in extreme situations (i.e. at catastrophe sites, under field conditions, etc.).

By solving this problem we started from the conception according to which the pins bored into the bones are put through the bores near the end parts of a fixing rod and the bores of two stretching tubes slidably mounted onto the end parts of said fixing rod, wherein the bores of both the fixing rod and the stretching tubes are larger in diameter than the diameter of the pins and are equidistantly spaced. Thereafter the fixing rod and the stretching tube are displaced—preferably axially—in relation to each other, hereby a shear force will be exerted to the pins. If the fixing rod and the stretching tube differ from each other in the hardness of their materials, the softer material—that is the material of the stretching tube—because of the hardness of the pin can be deformed—"smeared"—in the proximity of the bores receiving the pins, thus the area of "adhesion" will be enlarged meanwhile the shearing force remains constant. On the base of realizing the foregoing, a simple fixation of the unilateral groups of pins becomes possible.

The different quality and hardness of the materials of the fixing rod and the stretching tube—together with fixing the pins as described above—yielded an unexpected result. That is, the device constructed in this manner is not completely rigid, but "springs", dynamizes due to the loading of the pins. This dynamization is one of the primary requirements for healing.

Thus, the problem of the fixator described above has been solved according to the present invention as follows: the fixator comprises a fixing rod with equidistantly spaced and aligned bores, which bores receive the end parts of pins known per se drilled into the bone the diameters of said bores being larger than those of the pins; the above fixator further comprising two stretching tubes suitably mounted on the end parts of the fixing rod and provided with bores of similar diameter, spacing and position to those of the bore of the fixing rod, finally, an internally threaded closing piece shaped to facilitate the drawing is screwed on thread parts formed at the both ends of the fixing rod.

The material of the fixing rod and that of the closing piece can be aluminium-alloy—preferably an AlMgSi-alloy—the stretching tube, however, can be made of soft aluminium. The material of the stretching tube has always to be softer than that of the fixing rod. Naturally, the material of the pins is a stainless steel alloy, therefore being significantly harder than that of the fixator members.

The closing pieces may be provided with a corrugated surface near its outer, closed end part, for promoting the drawing and may also have one or more cross-bores.

In other embodiment of the present invention stretching tubes are slidably mounted onto the end parts of the above mentioned fixing rod comprising bores, which stretching tubes are provided with longitudinal slot holes with laterally reaching recesses having a self-locking angular arrangement with the longitudinal axis, the stretching tubes being further provided with a corrugated surface near the outer, closed end part and with one or more internal cross-bore(s).

In case of a further embodiment—suitable for treating fractures of the femur—bores near one of the end parts of the fixing rod enclose an angle of approximately 130° with the longitudinal axis, in order to directly receive the pins introduced into the femoral neck.

The external fixator according to the present invention forms a self-retaining, stressed and complex unit—does not contain any separate element—and provides a very simple and cheap outer frame meeting the desired biomechanical requirements. Fixation between pins and nails and the fixator can easily be carried out without using any special tools.

Because of its reasonable price the disposable form is preferred. By using the fixator according to the present invention the surgical technics become more simple and rapid. After having introduced the so-called "self-boring" pins, the fixator can immediately be mounted and easily fixed. Fixators mounted under field conditions or in a catastrophe situation can easily be removed when performing the definite treatment in a hospital and a new fixator can be applied following reposition.

The external, self-retaining, stressed fixator according to the invention is significantly lighter compared to the previously known frames therefore causes less inconvenience to the patient. The complete set contains a fixing rod and two stretching tubes with two closing pieces, an arm for driving in the pin and a suitable number of pins, all of them are, of course, sterilized before packing.

The fixator according to the present invention can be manufactured in several sizes—for use in case of various fractures and limbs—however, all of them function on the base of the same principle. The various dimensions of the fixator are determined by the diameters of the various pins, nails and wires and by the degree of the loading to be expected. It can be used for the treatment of the fractures of the forearm, upper arm, leg and femur, etc.

The bores aligned in the fixing rod may facilitate—as a pattern—the drilling in the nails and the pins. After having mounted the fixing rod—following the definite setting up—a stressed, self-retaining fixator can be produced without any displacement due to the shear force having an effect on the pins by tightening of the closing pieces. The displacement of the pins is also inhibited—in addition to the above mentioned shear force—by the large bearing surface.

BRIEF DESCRIPTION OF THE DRAWINGS

The present invention and its embodiments will further be illustrated by the accompanying drawings in which.

Figure 2:
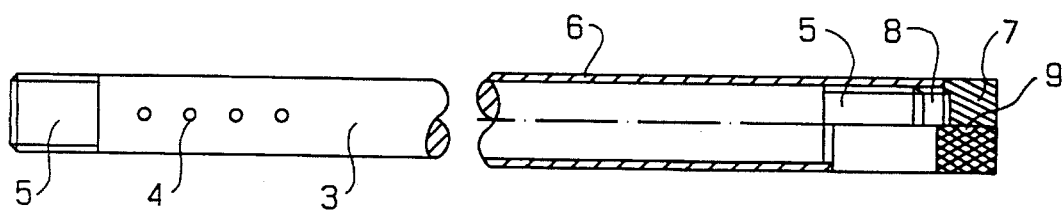
FIG. 2 illustrates the disposable fixator according to the invention where sectional views of the stretching tube—applied to the end part of the fixing rod—(see at the right side of the drawing), and that of the closing piece can be seen.
Figure 4:
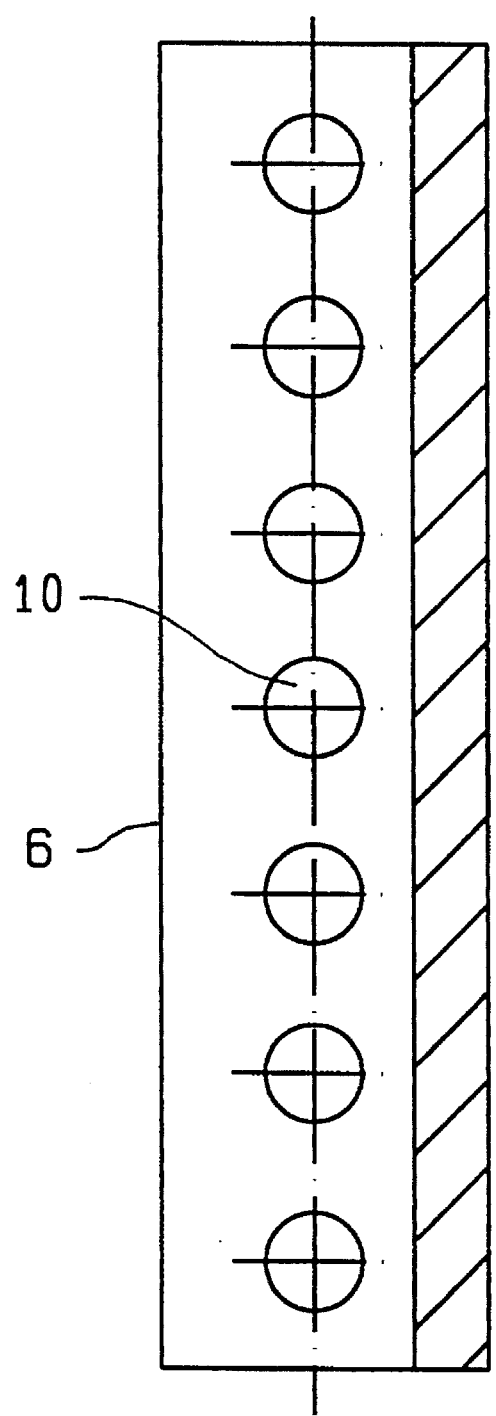
Figure 5:
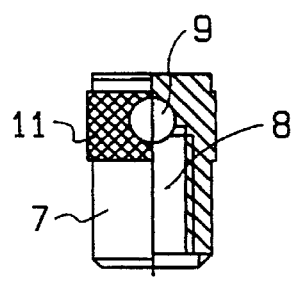
Figure 6:
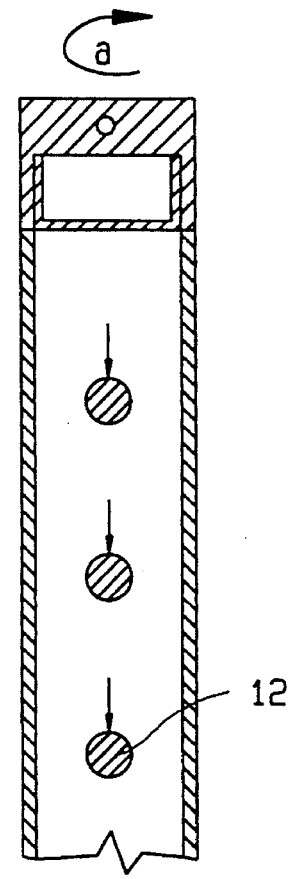
Figure 7:
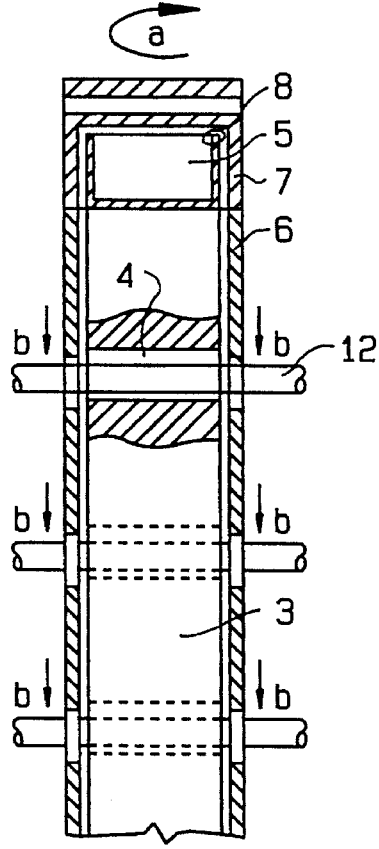
Figure 7A:
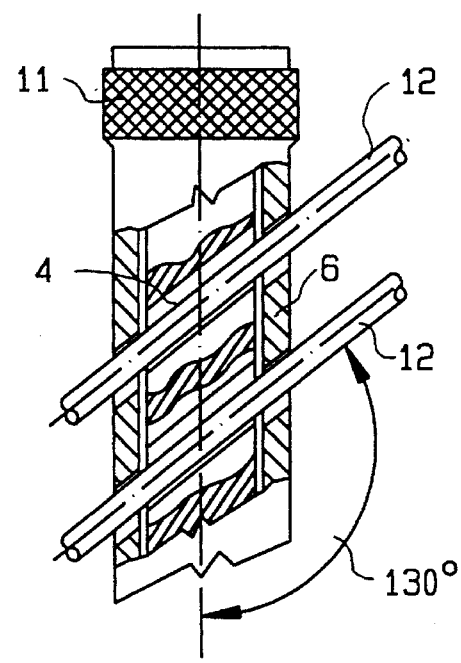
Figure 8:
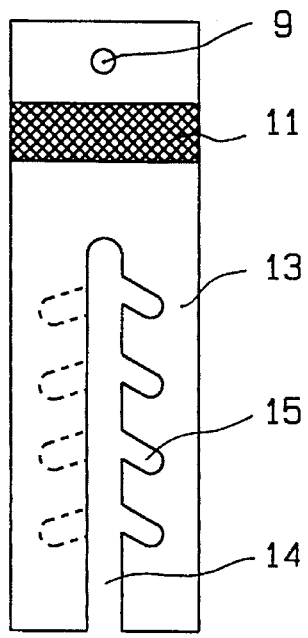
Figure 9:
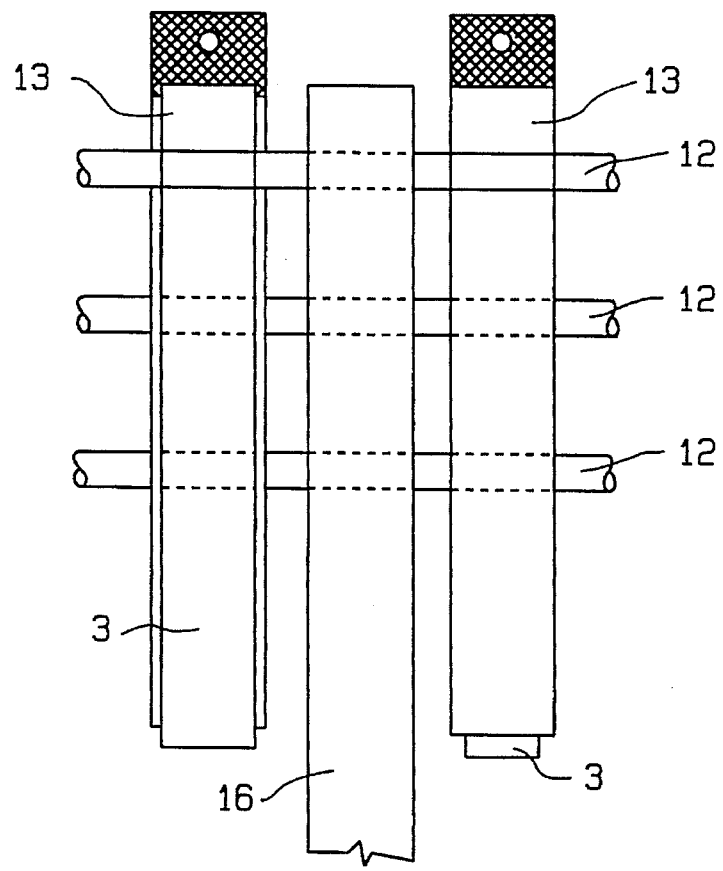

FIG. illustrates a fixator similar to that of FIG. 2 with the exception that the location of the bores of the fixing rod is different;

FIG. 4 shows the stretching tube partly in a side view and partly in a sectional view;

FIG. 5 illustrates the closing piece partly in a side view and partly in a longitudinal section;

FIG. 6 shows—in a schematic longitudinal view—the stretching—fixation principle of the fixator according to the invention;

FIG. 7 is a longitudinal view—turned off by 90°—of the schematic view seen in FIG. 6;

FIG. 7a shows another embodiment partly in a side view and partly in a sectional view on enlarged scale;

FIG. 8 shows a schematic front view of a further embodiment of the stretching tube; and FIG. 9 illustrates the embodiment according to FIG. 8, mounted on pins.

DESCRIPTION OF THE PREFERRED EMBODIMENTS

Figure 1:
FIG. 1 is a schematic front view of the fixing rod provided with aligned bores, of a well-known disposable fixator.

FIG. 1 shows the fixing rod 1 of an already known, disposable fixator with aligned bores 2. The pins placed into the fractured bones are introduced into the bores 2. (The pins are not shown.) Fixing of the pins in the bores 2 can be carried out as follows: the fixing rod 1—made of soft aluminium—is plastically deformed in the proximity of the bores 2 by using so-called sealing tongs, producing a strong joining between the fixing rod 1 and the pins. The fixing rod 1 and the pins. The fixing rod 1—made of soft aluminium—can easily be bent and formed, therefore the device can suitably be used for fixing small tubular bones.

FIG. 2 shows a preferred embodiment of the present invention. Fixing rod 3 comprises aligned bores 4 near its end parts where the number, diameter and the spacing of bores 4 are suitably selected. It is rather important that the diameter of the bores 4 should be significantly larger than that of the pins (not shown). The significance of the above-mentioned requirement will be explained in connection with FIGS. 6 and 7. At the right side of FIG. 2, near the end part of fixing rod 3, a stretching tube 6 is slidably mounted, the outer end surface of which bears against the inner front side of the closing piece 7 which can be screwed on the threaded end part 5 at the end of fixing rod 3.

Figure 3:
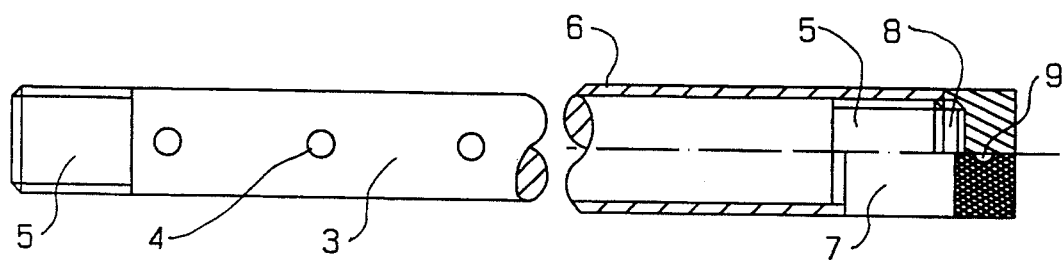

FIG. 3 differs from the embodiment shown in FIG. 2 only in dimensions and also in that the spacing of the bores 4 of the fixing rod 3 is larger. This embodiment can be used in case of larger bones—tibia and femur. In the latter case the bores 4 at one end part of the fixing rod 3 enclose an angle of 130° with the longitudinal axis of the fixing rod 3.

FIG. 4 shows the stretching tube 6 in a view and in a sectional view (at one part of FIG. 4). It can be seen that the wall of the stretching tube 6 contains aligned bores 10 which are similar to the bores 4 of the fixing rod 3 in diameter and spacing.

FIG. 5 shows the closing piece 7 comprising a longitudinally extending, internally threaded blind hole 8. The thread of the blind hole 8 naturally fits to the thread of the threaded part 5 of the fixing rod 3. The closing piece 7 has a corrugated surface 11 and near to its outer end (see the upper part of the drawing) and also a cross-bore 9 for a rod used for drawing.

FIGS. 6 and 7 show schematically the mode of stretching of the external fixator according to the invention in two views, partly in a sectional view. The pins 12 have a certain clearance in the bores 4 of the fixing rod 3 and in the bores 10 of the stretching tube 6, respectively. The closing piece 7 screwed on the threaded part 5 can be screwed and fastened by hand—by the aid of the corrugated surface 11—or by using a rod placed into the cross-bore 9. When screwing inwardly—in the direction of the arrow "a"—the closing piece 7, the stretching tube 6 will be shifted in the direction of the arrow "b", therefore the bores 4 and 10—displaced axially compared to each other—exert to the pins 12 a shear force, thus forming a very strong joining which can be ceased by screwing the closing piece 7 in a direction opposite to "a". Of course, it is also possible to form an embodiment where the fixing rod 3 is moved axially in relation to the stretching tube 6, also by the aid of the closing piece 7. In this case a somewhat different (not shown) construction has to be applied which—also by the effect of a shear force between the bores and the pins—can provide a strong fixation.

Finally, FIGS. 8 and 9 show another embodiment of the present invention in which the stretching tubes 13 are also slidably mounted onto the end parts of the fixing rod 3. The stretching tube 13 has a corrugated surface 11 and a cross-bore 9 in its outer end (shown at the upper part of the drawing). Along the stretching tube 13 can be found a slot hole 14, the inner end of which is open (shown at the lower part of the drawing). The slot hole 14 is provided with laterally reaching recesses 15 having a self-locking angular arrangement with the longitudinal axis. The dimensions of width of both the slot hole 14 and the recesses 15 are larger than the diameters of the pins 12. As can be seen in FIG. 9, the stretching tubes 13 are pushed onto the fixing rod 3, previously mounted on the pins 12. When pushing on the stretching tubes 13, the pins 12 move along the slot hole 14, thereafter—when turning the stretching tube 13 off—they take place in the recesses 15 and hereby they may become locked as a bayonet locking. In order to assure stability a smooth inside rod 16 provided by bores will also be applied.

For those skilled in the art it will be obvious that a number of other embodiments of the present invention different from those described in the preceeding may also be applied within the scope of the present invention. For example, the cross-section of the fixing rod 3 can be varied and may be modified along the length of the fixing rod 3 and the closing piece 7 can be provided by—for example—a hexagonal head for a fork spanner, etc.

We claim:

1. An improved disposable external fixator for fixing fractured bones comprising:
   a) an elongated member with a plurality of bores (4) disposed therein and skeletal pins (12) received in said bores for boring into said fractured bones for fixing them together, said elongated member being defined by a fixing rod (3) having a longitudinal axis and opposite ends with threaded end parts (5) and said bores (4) being spaced from each other and axially aligned and of predetermined diameter larger than that of said skeletal pins (12) received in them;
   b) a stretching tube (6) slideably mounted onto each of said opposite ends of said fixing rod (3) and provided with bores (10) of a diameter, spacing and position corresponding to at least some of the bores (4) in said fixing rod (3) whereby the skeletal pins (12) have a certain clearance in the bores (4) of the fixing rod (3) and in the bores (10) of the stretching tubes (6), respectively;
   c) a threaded closing piece (7) screwed onto each of said threaded end parts (5) of the fixing rod (3) and engageable with one of said stretching tubes (6) to axially move said stretching tube (6) relative to said fixing rod (3) upon threading of said closing piece (7) onto said threaded end part (5); and
   d) said stretching tubes (6) being made of soft aluminum, and the fixing rod (3) and the closing pieces (7) being made of an aluminum-alloy having more strength and hardness than said soft aluminum.

2. A disposable external fixator as claimed in claim 1, wherein the closing pieces (7) are provided with a corrugated outer surface (11) and with one or more through bores (9).

3. A disposable external fixator according to claim 1 wherein said bores (4) near to one of said opposite ends of the fixing rod (3) enclose an angle of approximately 130° with the longitudinal axis of said fixing rod (3).

4. An improved disposable external fixator for fixing fractured bones comprising:
   a) an elongated member with a plurality of bores (4) disposed therein and pins (12) received in said bores for boring into the fractured bones, said elongated member being defined by a single fixing rod (3) having a longitudinal axis and opposite ends and with said bores (4) being spaced from each other and axially aligned and having a diameter larger than the diameter of the pins (12) received in them; and
   b) a stretching tube (13) slidably and rotatably mounted onto each of said opposite ends of the fixing rod (3), each of said tubes (13) being provided with a longitudinal slot (14) with laterally extending recesses (15) having a self-locking angular configuration with respect to said longitudinal axis.

5. A disposable external fixator according to claim 4 wherein said stretching tubes (13) are each provided with a corrugated outer surface (11) and with one or more cross-bores (9).

6. An improved disposable external fixator for fixing fractured bones comprising:
   a) an elongated member with a plurality of bores (4) disposed therein and skeletal pins (12) having opposite ends, with one of said ends received in said bores (4) and the other of said ends disposed outwardly of said elongated member for boring into only one side of said fractured bones for fixing them together, said elongated member being defined by a fixing rod (3) having a longitudinal axis and opposite ends with a threaded end part (5) on at least one of said ends and said bores (4) being spaced from each other and axially aligned and of predetermined diameter larger than that of said skeletal pins (12) received in them;
   b) a stretching tube (6) slideably mounted onto said at least one of said opposite ends of said fixing rod (3) and provided with bores (10) of a diameter, spacing and position corresponding to at least some of the bores (4) in said fixing rod (3) whereby the skeletal pins (12) have a certain clearance in the bores (4) of the fixing rod (3) and in the bores (10) of the stretching tubes (6), respectively;
   c) a threaded closing piece (7) screwed onto said threaded end part (5) of the fixing rod (3) and engageable with said stretching tube (6) to axially move said stretching tube (6) relative to said fixing rod (3) upon threading of said closing piece (7) onto said threaded end part (5); and
   d) said stretching tube (6) being made of soft aluminum, and the fixing rod (3) and the closing piece (7) being made of aluminum-alloy having more strength and hardness than said soft aluminum.

7. An improved disposable external fixator for fixing fractured bones comprising:
   a) an elongated member with a plurality of bores (4) disposed therein and pins (12) having opposite ends, with one of said ends received in said bores (4) and the other of said ends disposed outwardly of said elongated member for boring into only one side of said fractured bones, said elongated member being defined by a single fixing rod (3) having a longitudinal axis and opposite ends and with said bores (4) being spaced from each other and axially aligned and having a diameter larger than the diameter of the pins (12) received in them; and
   b) a stretching tube (13) slideably and rotatably mounted onto at least one of said opposite ends of the fixing rod (3), said tube (13) being provided with a longitudinal slot (14) with laterally extending recesses (15) having a self-locking angular configuration with respect to said longitudinal axis.

* * * * *